United States Patent
Komatsu et al.

[11] Patent Number: 5,591,461
[45] Date of Patent: Jan. 7, 1997

[54] FORMING APPARATUS FOR A POWDERY SAMPLE

[75] Inventors: Takashi Komatsu; Hiroomi Uehara; Syuji Shinkai, all of Saitama-ken, Japan

[73] Assignee: Nisshin Flour Milling Co., Ltd., Tokyo, Japan

[21] Appl. No.: 385,506

[22] Filed: Feb. 8, 1995

[30]  Foreign Application Priority Data

Feb. 8, 1994 [JP] Japan ................................. 6-014478

[51] Int. Cl.⁶ ............................ B29C 43/00; G01N 33/02
[52] U.S. Cl. .................... 425/169; 73/73; 73/169; 425/225; 425/406; 425/409; 425/420
[58] Field of Search ..................... 425/169, 225, 425/406, 409, 420; 426/231; 100/214; 73/73, 169

[56]  References Cited

U.S. PATENT DOCUMENTS

| | | | |
|---|---|---|---|
| 3,966,973 | 6/1976 | Henry et al. | 426/231 |
| 4,715,212 | 12/1987 | Johanson | 73/38 |
| 5,162,103 | 11/1992 | Dechene et al. | 422/104 |

*Primary Examiner*—James P. Mackey
*Attorney, Agent, or Firm*—Townsend and Townsend and Crew LLP

[57]  ABSTRACT

A powdery sample forming apparatus, which is used for measuring a water content of powder and in which all operations from powder supply to powder discharge are automated, includes a vertically elongated housing which has a sample inlet port at an upper portion thereof and a sample discharge port at a lower portion thereof. A porous plate or a screen plate divides the housing into longitudinal compartments and a gate opens and closes a bottom portion of one of the divided compartments. A vertically movable press member in the compartment having the gate presses the sample against the gate. A window is formed in a side wall of the compartment having the gate and can be cleaned with air under pressure or a vacuum.

4 Claims, 2 Drawing Sheets

FORMING APPARATUS FOR A POWDERY SAMPLE

BACKGROUND OF THE INVENTION

1. Field of the Invention

The present invention relates to a forming apparatus for a powdery sample.

2. Description of the prior Art

A spectroscopic device, a hue meter, and the like are used for irradiating light on the surface of a powdery sample, e.g., flour, and receiving and measuring the light reflected by or transmitted through the sample, so that the nature of the sample, e.g., the component such as a water content, can be analyzed. It is important for measurement that the powdery sample is always presented to the devices with the same density and the same surface condition. To set the sample in such a condition is called forming of the powdery sample.

Conventionally, in the forming of the powdery sample employed for spectroscopic measurement, in order to obtain uniformity of the surface condition of the sample, the sample is placed in a shallow saucer-like container called a cell with a glass window on its bottom. The upper surface of the sample is uniformed by leveling, and the sample is pressed against the bottom of the cell, so that the surface condition of a portion of the sample facing the glass window is uniform. Usually, these forming operations are manually performed. Thus, an individual difference occurs in operation to cause a difference in surface condition from one sample to another, resulting in measurement error. Even if only the spectroscopic measurement operation can be automated, it is difficult to automate the entire forming operation.

SUMMARY OF THE INVENTION

The present invention has been made in view of the above situations, and has as one of its objects to provide a forming apparatus for a powdery sample in which all operations from supply of the sample to discharge thereof are automated.

In order to solve the above problems, according to the present invention, there is provided an apparatus for forming a powdery sample comprising: a vertically elongated housing which has a sample inlet port at an upper portion thereof and a sample discharge port at a lower portion thereof and the interior of which is divided into longitudinal compartments with a porous plate or a screen plate; a gate for opening and closing a bottom portion of one of the divided compartments; a press member vertically movable in the compartment having the gate for pressing the sample; a transparent window, e.g., a glass window, formed in a side wall of the compartment having the gate; and a unit for cleaning the window by injecting compressed air from the press member, or by suction.

This powdery sample forming apparatus can be directly connected to a bypass line when a powdery sample is to be extracted from a part of the powder conveying line, and can charge and use the sampled powder.

The upper and lower portions of the compartment having a gate may have identical sections. It is, however, preferable that the area of the section of the lower portion of this compartment be slightly larger than that of the upper portion because the powder can be discharged easily.

The pore diameter of pores of a porous plate or screen plate, mesh number employed, and material and shape of the porous plate or screen plate are determined in accordance with powder to be charged, and are not particularly limited.

A mechanism and method of opening and closing the gate are not particularly limited. The entire section can be preferably open when the gate is opened. As the mechanism for opening and closing the gate, a rotary actuator located outside the compartment, or a combination of a cylinder link and a lever may be employed. Other than this, another method may be employed wherein a lock mechanism is unlocked when the gate is to be opened, and the gate is opened by its own weight or a load, e.g., a spring, and is rotated in the opposite direction by its own weight, thus closing the gate.

A press member may have any shape as far as it can uniformly compress the powder. The press member has an air injection port for cleaning the window. However, the window may be cleaned by suction in place of air injection. In this case, a cleaner and a brush may also be mounted.

It is preferable that the gate has such a structure that the gate may be unlocked to be automatically opened when the powdery sample accommodated in the compartment having the gate is excessively compressed to indicate a different measurement value, or when the load acting on the gate surface exceeds a predetermined value, so that the powder will be prevented from being disabled to be discharged after measurement.

The powdery sample charged into the divided compartment fills the compartment having the closed gate, and an extra powder overflows from the upper opening of the compartment and drops. When a predetermined amount of sample filled in the compartment is pressed downward with the press member, the sample is compressed to form a uniform layer while part of air contained in the sample and part of the sample are discharged through the pores of the porous plate or the screen plate, so that a uniform sample surface is formed on an inner side of a transparent window, e.g., a glass window. When a predetermined amount of sample is compressed in this manner with a predetermined pressure, stable measurement can always be performed. Therefore, the accurate spectroscopic analysis (e.g., detection of a water content) of the sample can be performed by irradiating light from the spectroscope toward the sample surface and by receiving the light reflected by the sample surface. The transparent window, e.g., a glass window, can be cleaned by utilizing compressed air injected from the press member, or by suction air.

DETAILED DESCRIPTION OF THE INVENTION

A powdery sample forming apparatus according to the present invention will be described with reference to accompanying drawings.

Figure 1:
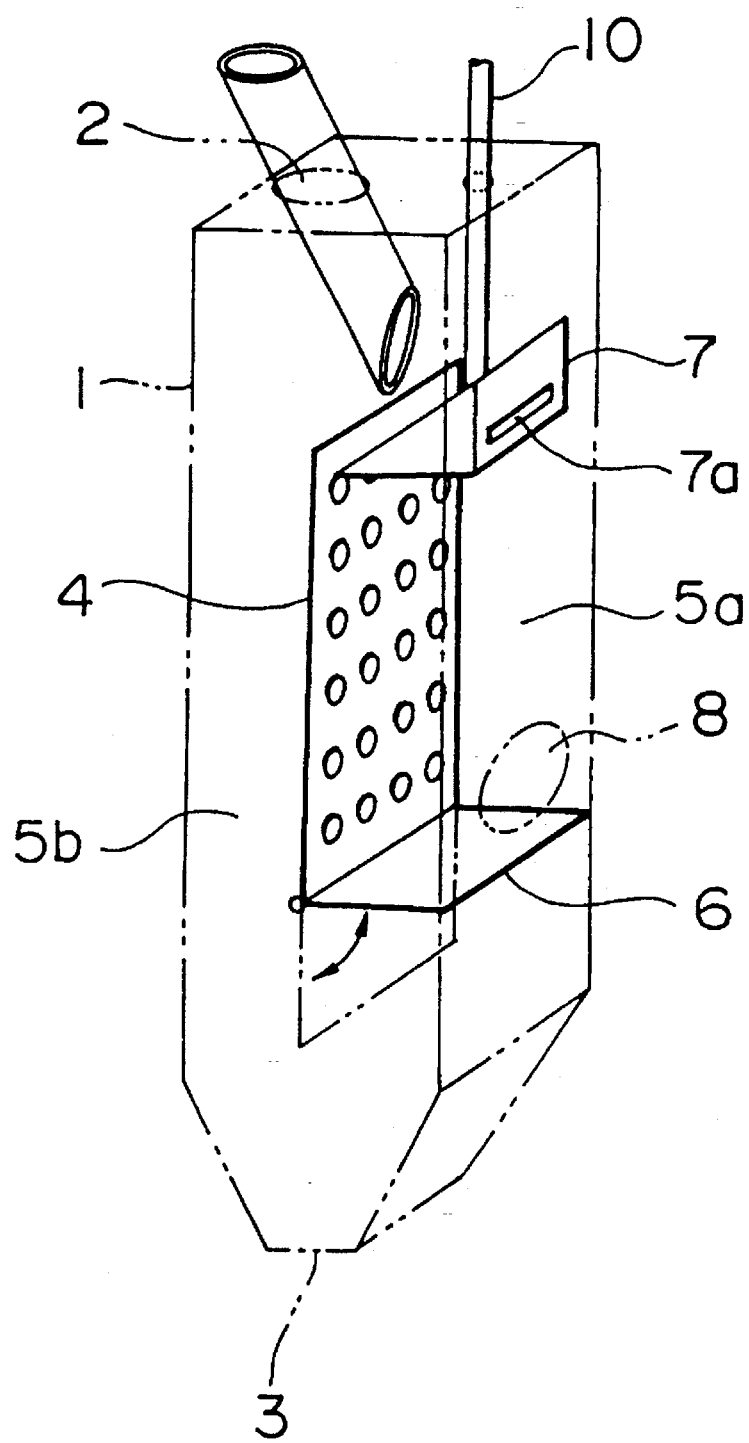
FIG. 1 is a perspective view showing the internal structure of a powdery sample forming apparatus according to the present invention.

FIG. 1 is a perspective view showing the internal structure of the powdery sample forming apparatus according to the present invention.

The housing of the powdery sample forming apparatus of the present invention forms a vertically elongated housing 1 and has a sample inlet port 2 and a discharge port 3 at its upper and lower portions, respectively. The interior of the housing 1 is divided with a porous plate or a screen plate 4 into longitudinal compartments. In the embodiment shown in FIG. 1, the interior of the housing 1 is divided into two compartments, i.e., an operational compartment 5a and an overflow compartment 5b. The porous plate or the screen plate 4 does not extend throughout the entire height of the interior of the housing 1, but spaces are kept above and below the porous plate 4 to allow operations of a gate 6 and a press member 7 (to be described later).

The gate 6 is mounted to open or close the lower opening of the longitudinal operational compartment 5a surrounded by the porous plate or screen plate 4 and the outer wall of the housing 1. The upper portion of the operational compartment 5a is open. Both the upper and lower portions of the overflow compartment 5b are open. The press member 7 interlocked with a piston-cylinder unit (not shown) fixed on the outer upper surface of the housing 1 through a rod 10 is mounted to be vertically movable in the operational compartment 5a. A window 8 fitted with synthetic quartz glass is formed in the outer wall of the operational compartment 5a. Compressed air from the outside flows through the hollow portion of the rod 10 and is injected from an injection port 7a formed in the side surface of the press member 7 toward the inner surface of the window 8, thus cleaning the window 8. A spectroscope 9 is installed outside the housing 1 opposite the window 8 as shown in FIGS. 2A to 2F.

The gate 6 is located in the lower portion of the operational compartment 5a, and is opened after a sample measurement operation is completed. The gate 6 is operated by an external rotary actuator (not shown).

The operation of the powdery sample forming apparatus according to the present invention having the above arrangement will be described with reference to the accompanying drawings.

FIGS. 2A, 2B, 2C, 2D, 2E, and 2F illustrate the operations of the powdery sample forming apparatus according to the present invention in an order of steps.

Figure 2A:
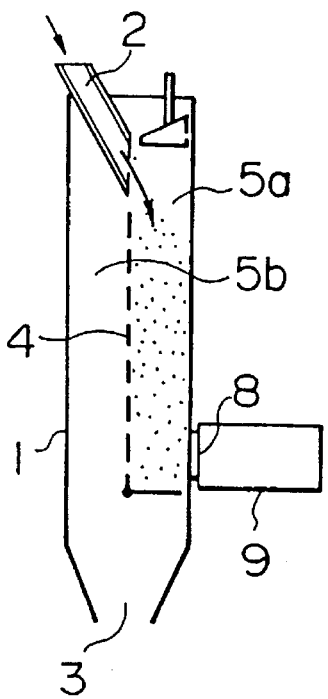
FIGS. 2A to 2F are views showing the forming operations of the powdery sample forming apparatus according to the present invention in an order of steps.

FIG. 2A shows a powdery sample charging step. The gate 6 is closed, and the press member 7 has been moved above the upper opening of the operational compartment 5a. The powdery sample sampled from an arbitrary manufacturing line through a bypass is charged from the sample inlet port 2 of the housing 1 to the upper opening of the operational compartment 5a. The sample is deposited on the gate 6.

Figure 2B:
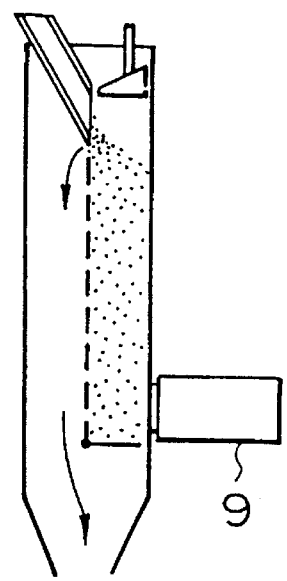

FIG. 2B shows a sample charge completion step in which the sample fills the operational compartment 5a to complete charging. An extra sample overflows from the upper opening of the operational compartment 5a and drops in the overflow compartment 5b, and is discharged to the manufacturing line through the sample discharge port 3 of the housing 1.

Figure 2C:
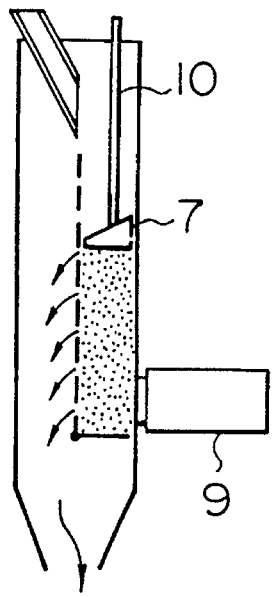

FIG. 2C shows a pressing step. The piston-cylinder unit is operated to move the press member 7 downward. The press member 7 continues downward movement while compressing the sample in the operational compartment 5a. A part of the compressed sample leaks through the pores or mesh pores of the porous plate or screen plate 4 and drops in the overflow compartment 5b. The press member 7 is stopped when it compresses the sample to a predetermined height.

Figure 2D:
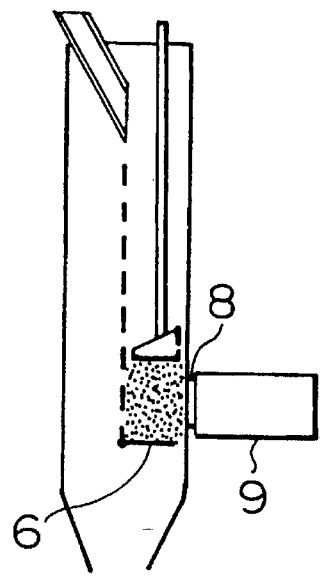

FIG. 2D shows a measuring step. The press member 7 is stopped at a predetermined position higher than the window 8. At this time, the spectroscope 9 is operated to measure the surface of the sample formed on the inner surface of the window 8. The spectroscope 9 calculates and displays the water content of the sample.

Figure 2E:
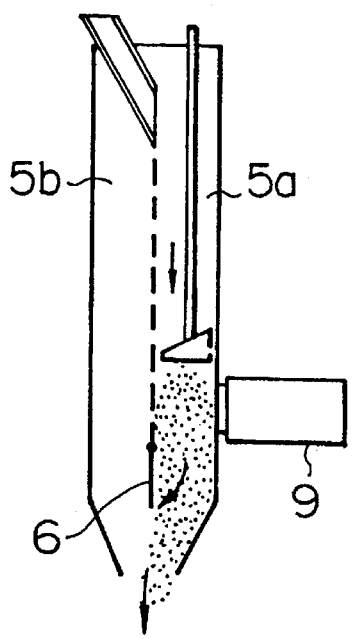

FIG. 2E shows a discharging step. When the gate 6 is opened, the sample in the operational compartment 5a is discharged. When the press member 7 is further moved downward, the remaining powdery sample in the operational compartment 5a is entirely discharged.

Figure 2F:
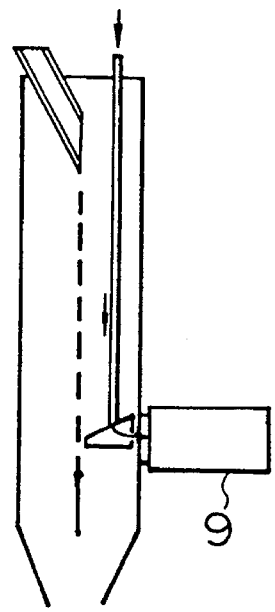

FIG. 2F shows a cleaning step. As it moves downward, the press member 7 injects compressed air from it toward the inner surface of the window 8, thus cleaning the window 8. When cleaning of the window 8 is completed, the press member 7 is moved upward to the uppermost position, and the gate 6 is closed, thus making preparation for a subsequent cycle.

As has been described above, according to the present invention, the powdery sample sampled from an arbitrary manufacturing line is charged into the operational compartment through its upper opening to fill it. An extra sample is caused to overflow into the overflow compartment. While the sample is being compressed with the press member, the extra particle sample is discharged through the mesh pores of the screen plate. As a result, a uniform sample layer solidified at a predetermined pressure in a natural state, hence, a constant, uniform surface which is leveled flat, is always formed on the inner surface of the window, and measured by a spectroscopic device. After the measurement, the window surface is always cleaned to maintain the purity of the sample. The sample after measurement is entirely discharged. Therefore, excellent effects can be obtained as follows:

(1) Since the density and surface condition of the sample are always constant, the sample can be accurately measured by the spectroscopic device.

(2) The entire operations from sample charge to discharge through measurement can be automatically performed without requiring any manual operations.

(3) Samples can be arbitrarily sampled from a large number of powder manufacturing plants, lines, and steps, gathered at one place, and subjected to adjustment, examination, and the like.

What is claimed is:

1. An apparatus for forming a powdery sample comprising:

a vertically elongated housing which has a sample inlet port at an upper portion thereof, a sample discharge port at a lower portion thereof, and a screen plate dividing an interior of the housing into longitudinal compartments;

a gate for opening and closing a bottom portion of one of said compartments;

a press member vertically movable in said compartment and cooperating with said gate for pressing the sample; and a window formed in a side wall of said compartment opened and closed by said gate.

2. An apparatus according to claim 1, further comprising a unit for cleaning said window by injecting compressed air against said window.

3. An apparatus according to claim 1 wherein the screen plate comprises a porous plate.

4. An apparatus according to claim 1 comprising a unit for cleaning said window by subjecting a surface of the window to a vacuum.

* * * * *